United States Patent [19]

Shiraki et al.

[11] Patent Number: 5,653,976

[45] Date of Patent: Aug. 5, 1997

[54] RECOMBINANT VARICELLA-ZOSTER VIRUS AND PROCESS FOR CONSTRUCTING SAME

[75] Inventors: Kimiyasu Shiraki, Toyama; Michiaki Takahashi, Osaka, both of Japan

[73] Assignee: The Research Foundation for Microbial Diseases of Osaka University, Osaka, Japan

[21] Appl. No.: 340,880

[22] Filed: Nov. 15, 1994

Related U.S. Application Data

[63] Continuation of Ser. No. 873,821, Apr. 27, 1992, abandoned.

[30] Foreign Application Priority Data

Apr. 26, 1991 [JP] Japan ................... 3-191340

[51] Int. Cl.$^6$ .................. A61K 39/25; A61K 39/29; C12N 15/86
[52] U.S. Cl. ................ 424/93.2; 435/91.41; 435/172.3; 435/320.1; 536/23.72
[58] Field of Search .................. 435/69.1, 172.1, 435/172.3, 320.1, 69.3; 424/93.1, 93.6, 93.2, 227.1, 229.1

[56] References Cited

U.S. PATENT DOCUMENTS 4,963,483  10/1990  Ellis et al. ........................ 435/69.3

FOREIGN PATENT DOCUMENTS 0251534  1/1988  European Pat. Off. .

OTHER PUBLICATIONS

"Varicella–Zoster Virus as a Live Vector for the Expression of Foreign Gene", Lowe et al., PNAS, vol. 84, pp. 3896–3900, Jun. 1987.

*Primary Examiner*—David Guzo
*Attorney, Agent, or Firm*—Wenderoth, Lind & Ponack

[57] ABSTRACT

The present invention provides a recombinant varicella-zoster virus prepared by inserting into the viral genome, nucleic acids from hepatitis B virus genome, a genomic DNA of the recombinant varicella-zoster virus, a live vaccine containing the recombinant varicella-zoster virus as an effective ingredient, an antigen derived from the recombinant varicella-zoster virus, and diagnostic agent containing the antigen. The recombinant varicella-zoster virus of the present invention can be utilized as a multivalent vaccine having an excellent immunity effect both on chickenpox and hepatitis B, and the expression products and genomic DNA thereof may be used as a multivalent diagnostic agent.

5 Claims, 3 Drawing Sheets

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 13 base pairs
        ( B ) TYPE: nucleic acid
        ( C ) STRANDEDNESS: double
        ( D ) TOPOLOGY: linear ( i i ) MOLECULE TYPE:

( i i i ) HYPOTHETICAL:

( i v ) ANTI-SENSE:

( v ) FRAGMENT TYPE:

( v i ) ORIGINAL SOURCE:
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY:
        ( B ) CLONE:

( v i i i ) POSITION IN GENOME:
        ( A ) CHROMOSOME/SEGMENT:
        ( B ) MAP POSITION:
        ( C ) UNITS:

( i x ) FEATURE:
        ( A ) NAME/KEY:
        ( B ) LOCATION:
        ( C ) IDENTIFICATION METHOD:
        ( D ) OTHER INFORMATION:

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO:

( x i ) SEQUENCE DESCRIPTION: SEQ ID NO:1:

AAACATGTCA ACG                      1 3

( 2 ) INFORMATION FOR SEQ ID NO:2:

( i ) SEQUENCE CHARACTERISTICS:
        ( A ) LENGTH: 13 base pairs
        ( B ) TYPE: nucleic acid
        ( C ) STRANDEDNESS: double
        ( D ) TOPOLOGY: linear ( i i ) MOLECULE TYPE:

( i i i ) HYPOTHETICAL:

```
        ( i v ) ANTI-SENSE:

( v ) FRAGMENT TYPE:

( v i ) ORIGINAL SOURCE:
                ( A ) ORGANISM:
                ( B ) STRAIN:
                ( C ) INDIVIDUAL ISOLATE:
                ( D ) DEVELOPMENTAL STAGE:
                ( E ) HAPLOTYPE:
                ( F ) TISSUE TYPE:
                ( G ) CELL TYPE:
                ( H ) CELL LINE:
                ( I ) ORGANELLE:

( v i i ) IMMEDIATE SOURCE:
                ( A ) LIBRARY:
                ( B ) CLONE:

( v i i i ) POSITION IN GENOME:
                ( A ) CHROMOSOME/SEGMENT:
                ( B ) MAP POSITION:
                ( C ) UNITS:

( i x ) FEATURE:
                ( A ) NAME/KEY:
                ( B ) LOCATION:
                ( C ) IDENTIFICATION METHOD:
                ( D ) OTHER INFORMATION:

( x ) PUBLICATION INFORMATION:
                ( A ) AUTHORS:
                ( B ) TITLE:
                ( C ) JOURNAL:
                ( D ) VOLUME:
                ( E ) ISSUE:
                ( F ) PAGES:
                ( G ) DATE:
                ( H ) DOCUMENT NUMBER:
                ( I ) FILING DATE:
                ( J ) PUBLICATION DATE:
                ( K ) RELEVANT RESIDUES IN SEQ ID NO:

( x i ) SEQUENCE DESCRIPTION: SEQ ID NO:2:

AAACATGTCC GGA                                                  1 3
```

RECOMBINANT VARICELLA-ZOSTER VIRUS AND PROCESS FOR CONSTRUCTING SAME

This application is a continuation of now abandoned application, Ser. No. 07/873,821, filed Apr. 27, 1992.

FIELD OF THE INVENTION

The present invention relates to a recombinant varicella-zoster virus and a process for constructing same, the recombinant varicella-zoster virus thus obtained and the antigens and genomic DNA thereof being applicable as a vaccine, an immunological diagnostic agent, a genetic diagnostic agent, and a genetic engineering reagent.

PRIOR ART

The technology for constructing a recombinant virus by inserting foreign genes or heterogenes into viral genes, i.e., the technology to use the viral genome as cloning and/or expression vector has been employed since 1979, for example, in the production of rabbit β-globin using SV40 as a viral vector [Nature (London), 277, 108–114, 1979, ibid., 258, 35–40, 1979]. In 1980, the general meeting of the World Health Organization (WHO) declared extermination of smallpox based on the successful results of vaccine and recommended abolition of vaccination. Since then, the effective use of vaccinia virus which is an attenuated virus forming an effective ingredient of vaccination has attracted general attention throughout the world and is revaluated at present. Under such circumstances, a recombinant vaccinia virus created for the purpose of utilizing said viral genome as the cloning and expression vector of foreign genes has been reported [Proceedings of National Academy of Science (USA), 79, 4927–4931, 1982; ibid., 79, 7415–7419, 1982]. In addition, the ad hoc consulting group for WHO adopted a research-promoting plan for a recombinant virus vaccine using vaccinia virus, etc as a vector. [Nature (London), 312, 299, 1984]. This WHO proposal suggests: developing a viral vector such as a vaccinia virus vector with a wider host range which can utilize a higher animal cell as a host, with a view to solving the drawback of the conventionally used plasmid vector, phage vector and cosmid vector with a narrow host range(mainly bacteria or yeasts); and developing a multivalent vaccine using, as an effective ingredient, a recombinant virus constructed by inserting at least two kinds of foreign genes into vaccinia virus genome in place of the conventional combined vaccine comprising two or more kinds of antigens or heteroviruses. With the above-mentioned WHO declaration and proposal as the starting point, fundamental research and development efforts regarding viral vectors have actively been made in various fields, and as result, a huge volume of data has already been accumulated. More particularly, viral genomes already known to serve as such viral vectors include, for example, papillomavirus, polyomavirus, adenovirus, retrovirus, vacuolovirus, herpes simplex virus, Marek's disease virus, varicella virus, parbovirus, cauliflower mosaic virus, tobacco mosaic virus, and tomato golden mosaic virus [Virus, 36, 1–41, 1986; ibid., 37, 1–40, 1987; "Current Communication in Molecular Biology: Viral Vector," pp. 10198, Y. Olusman and S. H. Hughes (ed.), Cold Spring Harbor Laboratory (USA) pub. 1988, European Patent Provisional Publication No. 334,530].

From among the above-listed viral vectors, the varicella-zoster virus (hereinafter abbreviated as "VZV") related to the present invention is described below.

VZV is usually a cell-associated virus, the infectivity of which can be maintained only within live cells, so that it is difficult to separate the virus and subculture and mass-produce it in a test tube. There has therefore been a general tendency to be hesitant not only about making efforts to develop a VZV vaccine and diagnostic agents but also about fundamental and clinical research efforts on VZV as a pathogen of chicken pox. Progress of studies on VZV has therefore been very slow until the establishment of the cell-free Oka strain of attenuated VZV for live varicella vaccine by the present inventors in 1975 (Biken Journal, 23, 53–55, 1975; Japanese Patent Publication No. 51-19,018, Japanese Patent Publication No. 53-41,29; Japanese Patent Publication No. 56-42,144). Taking advantage of the development of a live vaccine using the above-mentioned Oka strain of attenuated VZV, fundamental and clinical research and applied research efforts on VZV have actively been carried out at various localities in the world. The live varicella vaccine using his Oka strain of attenuated VZV as the effective ingredient is thus now widely applied in practice throughout the world [Requirements for Varicella Vaccine (Live) Adopted 1984; WHO Technical Report Series, No. 725, pp. 102–124, 1985]. A huge volume of data regarding fundamentals, clinical, diagnosis and immunology of VZV has already been accumulated ["Virology," vol. 2, pp. 2011–2054, B. N. Fields, et al. (ed.), Raven Press (USA), pub. 1990]. Particularly, progress in the structural analysis of VZV genome has made great strides since the beginning of the 1980s through restriction mapping and total base sequence determination of VZV genome DNA, along with the development and diffusion of the technique for cloning of genes and expression thereof, and monoclonal antibody (Journal of General Virology, 67, 1759–1816, 1986; ibid., 67, 1817–1829, 1986; Virus, 37, 71–80, 1987). Some major virological findings as to VZV as derived from the references as referred to above are as follows.

VZV has an envelope, is a DNA-type virus taxologically falling within the herpes simplex virus group, i.e., herpesviridae, alphaherphesvirinae, and has a dia. of approximately 180 to 200 nm. This genome consists of a linear DNA having two chains of approximately 120 kilobase (kb), and is contained in a doughnut-shaped core having a dia. of approximately 75 nm within the nucleocapsid. This genomic DNA comprises an unique sequence (U) consisting of a long segment ($U_L$) and a short segment ($U_S$), a terminal repeat sequence (TR) consisting of $TR_L$ and $TR_S$ adjacent to $U_L$ and $U_S$, respectively, and an inverted repeat sequence (IR) consisting of $IR_L$ and $IR_S$ complementary to $TR_L$ and $TR_S$, respectively. These six segments are arranged in the direction from 5' toward 3' end in the order of $TR_L$, $U_L$, $IR_L$, $IR_S$, $U_S$ and $TR_S$. Currently, 71 ORFs (open reading frames) in total are numbered from 1 to 71 starting from the 5' end, and from among these genes, functions of the following 21 ORFs are identified or estimated [the figures in parentheses representing the ORF Nos.]: (4) early protein, (8) deoxyurinetriphosphatase, (10) trans-inducible protein, (13) thymidine synthetic enzyme, (14) glycoprotein (hereinafter abbreviated as "gp") V, (18) polynucleotide reductase small subunit., (18) polynucleotide reductase large subunit, (28) DNA ligase, (29) DNA-binding protein, (31) gp II, (36) thymidine kinase (hereinafter abbreviated as "tk"), (37) gpIII, (40) capsid protein, (48) exonulease, (62, 71) early protein, (63, 70) early protein, (66) protein kinase, (67) gpIV, and (68) gpI.

The following recombinant VZVs constructed by using VZV as a viral vector are known: a recombinant VZV obtained by inserting a foreign gene into the downstream region of the gpI promoter gene of VZV, the foreign gene being gp 350 of Epstein-Barr virus (Japanese Patent Provisional Publication No. 12,277/88 or European Patent Provisional Publication No. 251,534; Japanese Patent Provisional Publication No. 141,589/88; Journal of Virology, 61, 1796–1867, 1987); one having preS2 of hepatitis B virus (hereinafter abbreviated as "HBV") and surface antigen (hereinafter abbreviated as "HBs") gene (Japanese Patent Provisional Publication No. 12,277/88 or European Patent Provisional Publication No. 251,534) as foreign genes; a recombinant VZV prepared by combining gp300 and gp220 genes of Epstein-Barr virus into the downstream of the VZV gpI promoter gene and inserting further the resultant gene fragments into VZV tk gene so that the Epstein-Barr virus genes may be expressed as fusion protein with tk [Proceedings of National Academy of Science [USA], 84, 3896–3900, 1087; "ULCA Symposia on Molecular Biology; New Series, vol. 84: Technical Advances of Vaccine Development," pp. 235–241, by R. W. Ellis, at al., Alan R. Liss, Inc. (USA) pub. 1988]. However, all these recombinant VZVs are low in immunogenicity, and the safety and effectiveness thereof have not as yet been confirmed. No attempt has been reported to the present of putting on the market any vaccines or diagnostic agents prepared using these VZVs as antigens. The recombinant VZVs have not yet reached the level of practical application.

The conceivable reasons are as follows: (1) as compared with a virus of small size having usually a genome length of approximately 10 kb, a VZV is large with a very long infectious genome length of approximately 120 kb, and such a long DNA chain is susceptible to breakage and is therefore unstable; (2) a VZV, which is originally a cell-dependent virus, very unstable to heat, requires storage at a temperature lower than −60° C. for retaining the level of infectivity, and handling, culturing and mass production thereof are not easy; and (3) the number of produced infectious viral particles per cell in viral culture, which is approximately 10 to 100 particles for the other viruses, is as low as approximately 0.1 particle for VZV, leading to a very low production yield. For these reasons, it is very difficult to prepare or clone a genomic DNA of VZV which is suitably applicable not only for mass production of the genomes through VZV culturing but also in the test and research stage, and there is only a very low probability of screening a recombinant VZV eligible for industrial use in quality as well as in quantity. That is, the establishment of a recombinant VZV requires overcoming these very difficult conditions.

SUMMARY OF THE INVENTION

The objective of the present invention is to provide a novel recombinant VZV having a high expression ability of foreign genes inserted therein and a genetic stability of such ability through succeeding generations, and being safe and effective as an ingredient of a live vaccine. More particularly, the objective of the present invention is to provide a recombinant VZV carrying HBV genes which were particularly difficult to culture and mass-produce with other host-vector systems, from the point of view of practical use.

The present invention provides a recombinant VZV constructed by inserting at least one kind of gene selected from a gene group of HBV genome into a downstream region of a promoter gene of VZV and a process for constructing same.

The present invention also provides a genomic DNA of the above-mentioned recombinant VZV, a live vaccine containing this recombinant VZV, an antigen derived from this recombinant VZV, and diagnostic agents containing this antigen.

DETAILED DESCRIPTION OF THE INVENTION

Figure 1:
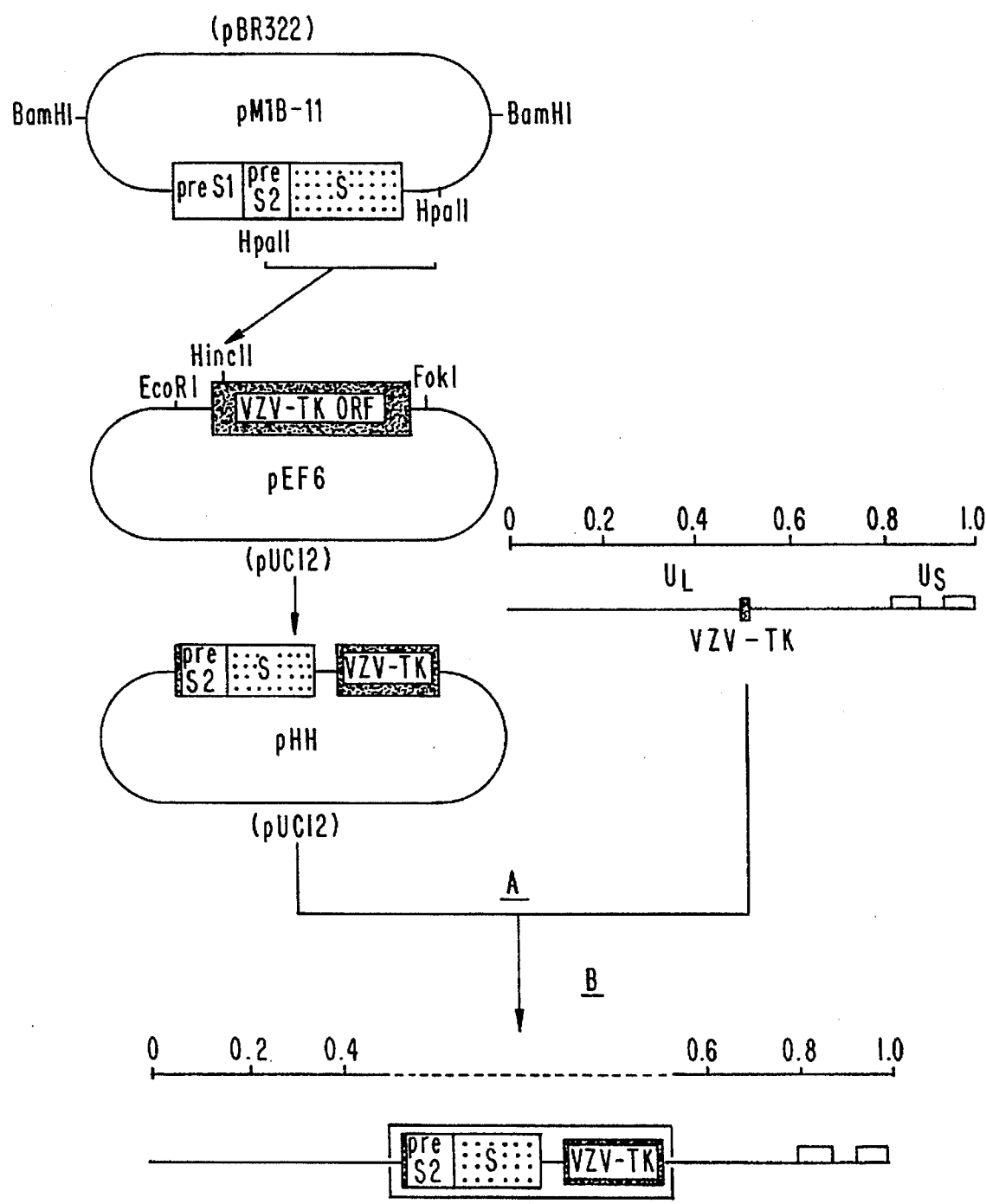
FIG. 1 is a schematic representation of the construction of a recombinant VZV of the present invention. The process A is cotransfection of VZV DNA and chimeric plasmid DNA (pHH), and B is recombination screening by IFA test.

The configuration and preferred embodiments of the present invention are as follows.

VZV strain as a viral vector in the present invention, which has as a main object to create a recombinant live vaccine excellent in safety, effectiveness and uniformity, the VZV genome is used as a vector. According to the present invention, any of such existing known VZV strains as those of Oka (ATCC VR-795), Webster (ATCC VR-916), Ellen (ATCC VR-586), YS, YG, SCO11, Kawaguchi and Dumas (Journal of General Virology, 67, 1816–1829, 1986; Virus, 37, 71–80, 1987) and VZV strains to be isolated may be used. From among these VZV strains, it is preferable to use an attenuated VZV strain with a view to ensuring a high safety in handling during test and research and during manufacture, and achieving industrial use including supply of a live vaccine and diagnostic agents excellent in both safety and effectiveness. Particularly from the point of view of the main object of the present invention presented above, the Oka strain of attenuated VZV, which is the only DNA-type attenuated virus established and publicly recognized worldwide for excellent safety and effectiveness, and currently employed throughout the world, is most suitable for the present invention.

Culture of VZV and selection of cells

Any of the conventional cells having a known sensitivity to VZV derived from human, monkey and Guinea pig may be used. From among these cells, on account of the probability of mixture of aberratic and caricinogenic factors, the eligibility as cells for culture of viral strain for vaccine, and the quantity of produced viruses, it is desirable to use human diploid cells such as HEL299 (ATCC No. CCL 137), MRC-5 (ATCC No. CCL 171), and WI-38 (ATCC No. CCL 75) publicly recognized for the manufacture of live vaccines. As the culture medium for multiplication and maintenance of these cells and for culturing viruses, a commercially available synthetic culture medium such as 199 Culture Medium

[manufactured by Difco Co. (USA)], or MEM Culture Medium [manufactured by Gibco Co. (USA)] may be used. Such a culture medium is applied for culturing by adjusting pH to approximately 6.8 to 8.0 through drop addition and mixture of approximately 7% (w/v) aqueous solution of NaHCO$_3$, and then adding fetal bovine serum [for example, that manufactured by Flow Co. (USA)] so as to achieve a final concentration of approximately 2 to 15% (w/v) immediately before use. VZV is cultured on a maintenance culture medium after inoculating a seed virus to previously prepared cell culture. The recommended temperature for culturing is within the range between 25° to 40° C., or more preferably, within the range of from 33° to 38° C.

Selection of VZV gene into which HBV genes are to be inserted

Theoretically, according to the present invention, all the above-mentioned 71 VZV genes can be used as portions into which HBV genes are to be inserted, respectively. Precautions to be taken in this use are to insert an HBV gene into the ORF region located in the downstream of the promoter gene thereof so as to permit functioning of the promoter gene, and to accomplish insertion without destroying the mutual codons of the VZV Gene and the foreign gene so as to ensure smooth translation. In general, since a viral gene into which a foreign gene has been inserted may be destructed and become unable to perform its original functions, it is desirable to adopt, as the promoter gene for combination of HBV gene, a gene which does not exert an influence on infectivity and multiplication of virus and has high expression ability with a strong promoter intensity, such as tk gene or gp gene. Particularly when using Oka strain of attenuated VZV as a viral vector, as the lack or the degradation of expression ability of the gpV gene (14th ORF) is known (Journal of Virology, 64, 4540–4548, 1990), use of this gene region cannot be recommended for an insertion site. It is however possible to use the gpV gene of a wild-type VZV; by inserting an HBV gene into the downstream of the promoter gene thereof, it is possible to cause destruction of the gene region encoding said gpV or to decrease the amount of expression. The recombinant VZV obtained therefrom is expected to show a very high usefulness as an attenuated strain similar to that of the Oka strain of attenuated VZV.

Selection of HBV genes to be inserted into VZV genome

Theoretically, according to the present invention, it is possible to use, as foreign genes to be inserted, one or more kinds of gene selected from the gene group of HBV genome to the extent of not deteriorating multiplication and infectivity of VZV. It is however necessary to be careful to prevent the gene regions from encoding toxic substances, or from detrimental substances and toxins involved in foreign genes, with due regard to the use of the recombinant VZV as a live vaccine. For example, both the preS1 region of HBV and a part of the preS2 region which is a polymerized human serum albumin receptor are known to have a high tropism for hepatic cells. When using a portion near the gene encoding any of these regions as a foreign gene, therefore, it is necessary to eliminate said region by means of a restriction enzyme. The recombinant VZV into which HBV genes have thus been inserted possesses antigenicity and immunogenicity for both HBV and VZV, as it is an attenuated strain, it is applicable in practice as an effective ingredient of a divalent live vaccine capable of providing immunity simultaneously against hepatitis B and chickenpox, and as a divalent antigen for diagnosis comprising both HBV and VZV antigens. It should particularly be noted here that, in the present invention, it is possible to put to practical use, as a live vaccine, an antigen available only as an inactivated vaccine in the conventional technology, such as an HBV antigen.

Construction of recombinant VZV

This process may be accomplished in the following sequence of steps: cloning VZV genes into which foreign genes are to be inserted; cloning the foreign genes; preparing chimeric plasmid formed by inserting the foreign genes into the thus cloned VZV gene; and constructing a recombinant VZV through recombination between his chimeric plasmid and the VZV genome. These steps are described below in this order.

(1) Cloning of VZV gene: After extracting and purifying VZV genomic DNA from cells infected therewith in the manner as described in Example 1 presented later, this DNA is digested by means of restriction enzymes, and these DNA fragments prepared through fractionation by the application of the conventional agarose gel electrophoresis are cloned with the use of a commercially available or known host-vector system (P. H. Powels, "Cloning Vector—A Laboratory Manual," 2 vols., Elsevier, 1985; "ATCC Recombinant DNA Materials," American Type Culture Collection, 1989). It is possible to clone, for example, VZV tk gene by inserting an H fragment prepared through digestion of a VZV genome with restriction enzyme SacI (Intervirology, 29, 301–310, 1988) into the SacI site of E. coli plasmid vector pUC12 [Methods in Enzymology, vol. 101, pp. 20–78, Academic Press (USA), 1983] and then introducing the plasmid to E. coli JM 109 strain (ATCC No. 53323) for transformation. An already cloned VZV gene (for example, journal of General Virology, 67, 1817–1829, 1986) may be utilized for simplifying this process.

(2) Cloning of HBV gene: Solution with a detergent or a ultrasonic waves of extracted cells of HBV-infected tissue or cultured HBV-infected cells; supernatant of viral culture or blood of an infected subject may be used as a starting material. A combination of known methods may be used for purifying he material. A purified fraction of virus particles is first prepared from the starting material by the use of a combination of, for example, the ammonium sulfate salting-out method, low-speed centrifugation, and/or the density gradient ultracentrifugation. Extraction and purification of genomic DNA from this purified fraction should preferably be carried out at a pH of 3 to 10 avoid irreversible denaturation thereof, and may be conducted by the conventional method. Genomic DNA may be prepared by adopting an appropriate combination of, for example, the heat/salt method using NaCl solution at 100° C., the detergent method using SDC (sodium deoxycholate) or SDS (sodium dodecylsulfate), the phenol extracting method based on the principle of dipbasic distribution, the guanidine chloride method using a concentrated liquid of guanidine chloride, the alkali method applied at a pH of approximately 10 with the use of NaOH solution or Na$_2$CO$_3$—NaHCO$_3$ buffer solution, and/or the alcohol precipitation method using cold ethanol. This DNA can be cloned in the same manner as in (1) above. To simplify the process, an already cloned HBV gene may be employed. For example, the HBV preS1-preS2-HBs antigen gene cloned in pM1B11 [Japanese Patent Provisional Publication No. 22,098/88 (Biken No. 1081)] is applicable.

(3) Preparation of chimeric plasmid of VZV-HBV gene: The downstream region of the VZV gene within the plasmid vector prepared in (1) above is digested with restriction enzyme, the DNA fragment derived from the HBV gene cloned in (2) above is then inserted into the restriction site of said plasmid vector, and this plasmid is transfected to the host cell for transformation. A chimeric plasmid is thus constructed with linkage Between the VZV gene and the HBV gene.

(4) Construction of recombinant VZV: A recombinant VZV is constructed by introducing simultaneously the DNA fragment of VZV genome in (1) above and the chimeric plasmid prepared in (3) above into the host cell to cause recombination therewith. For the introduction of the DNA fragment and the chimeric plasmid DNA into host cells, any of the known methods including the DEAE dextran method, the electroporation method and/or the calcium phosphate method is applicable. In the case of the calcium phosphate method (Virology, 52,485–467, 1973), coprecipitate of both DNAs is prepared coexistently with phosphate ions and calcium ions, and then the coprecipitate is brought into contact with the cell culture to cause cotransfection. Coprecipitate of calcium phosphate with chimeric plasmid DNA is brought into contact by drop addition of infected cells cultured for a period of approximately two to three hours by previously inoculating the VZV parental strain, thus introducing said DNA into VZV-infected cells. Then, a recombinant VZV can be created by culturing these cells, and causing recombination within this culture system between the VZV genomic DNA and the chimeric plasmid DNA.

(5) Recombinant VZV and culture thereof: All the various recombinant VZV clones available in the present invention are attenuated VZV strains and applicable as an effective ingredient of a live vaccine. For example, recombinant VZV clones between VZV and HBV genes are generically named as rVH Oka strain series, as disclosed in Example 6 presented later, and consist of the following 20 named strains: rVH1 Oka strain, and rVH2, rVH3, rVH4, rVH5, rVH6, rVH7, rVH8, rVH9, rVH10, rVH11, rVH12, rVH13, rVH14, rVH15, rVH16, rVH17, rVH18, rVH19 and rVH20 Oka strains. The recombinant VZV of the present invention may be obtained by inoculating a recombinant VZV seed virus into a cultured cell in the same manner as in Example 1 presented later and culturing same. In the culture supernatant and infected cells, there are produced, in addition to infectious recombinant VZV particles, various antigens which are the expression products of recombinant VZV genome. For example, by culturing the above-mentioned rVH7 Oka strain which was deposited under the Budapest Treaty in the European Collection of Animal Cell Cultures (ECACC) whose address is PHLS Centre for Applied Microbiology, Portion Down, Salisbury Wilts, SP4 OJG, U.K., on Apr. 15, 1992 and registered as rVH17-5 'Oka' strain (Provisional Accession No. V92041523), HBs polypeptides having molecular weights of 30 k, 35 k, etc. are produced in the culture supernatant, and HBs polypeptides of 26 k, 30 k, etc., in the infected cells, in addition to recombinant VZV particles. All these antigens and viral particles produced in the culture product of recombinant VZV and DNA thereof are applicable as vaccines, immunological diagnostic agents, generical diagnostic agents or genetic engineering reagents.

Restriction enzyme analysis of recombinant VZV genomic DNA

Analysis is possible by a conventional method such as the southern blot method (Journal of Molecular Biology, 98, 503, 1975). More specifically, a DNA fragment prepared through digestion of a VZV genome by means of restriction enzyme is fractioned by agarose gel electrophoresis, and these fractions are transferred onto a nitrocellulose membrane. Then, hybridization is applied between a fraction and a probe serving as an indicator with RI (radioisotope) to analyze the reaction image of the thus treated fraction by autoradiography.

Measurement, detection and identification of recombinant VZV antigen

Measurement, detection and identification of the viral particles and the various antigens produced by the recombinant VZV culture may be conducted by any of the conventional methods usually applied in immunology and serum diagnosis, such as the RPHA (reversed passive hemagglutination) method using red blood cells coated with an antibody; the ELISA (enzyme-linked immunosorbent assay) or the EIA (enzyme immunoassay) using an antibody labeled with enzyme, the RIA (radio immunnoassay) using an antibody labeled with RI, the immunofluorescence method consisting of dyeing infected cells with an antibody labeled with FITC (fluorescein isothiocyanate) and determining the presence of an antigen through a fluorescent microscope, and the immuno precipitation method comprising fractionating the immuno precipitation reaction product between an RI-labeled antigen prepared by culturing a recombinant VZV n a culture medium made by adding and mixing RI-labeled medium ingredients, on the one hand, and a previously prepared antibody, on the other hand, according to the extent of molecular weight through SDS-PAGE (SDS-polyacrylamide gel) electrophoresis, then analyzing the electrophoresis profile by autoradiography. To simplify this process, any of various commercially available measuring kits may be used. The antigen density can be measured by a conventional method such as the density gradient, equilibrium method. The shape of antigen particles may be observed by means of an electron microscope.

Measurement of infectivity of recombinant VZV

Any of the following conventional methods may be adopted; the CPE method of determining CPE (cell denaturation effect) with the rounding of infected cells as the indicator by means of an optical microscope; the plaque assay comprising visually counting PFU (plaque-forming unit) with each plaque as a unit, which is formed by culturing infected cells overlaid by solid culture media containing neutral red and agarose; the plaque assay consisting of visually counting PFU by dyeing infected cells fixed with formalin with methylene blue solution; and the focus method or counting FFU (focus-forming unit) which represents the number of focuses formed by infected cells by means of an optical microscope.

Cloning of recombinant VZV

Any of the conventional methods may be adopted, such as the focus method for cloning of infected cells, and the plaque assay for cloning of recombinant VZV. For sampling focuses and plaques, any of glass, plastic, and metal fine cylindrical tubes or cylinders may be used. The cloned infected cells and recombinant VZVs are inoculated to new cell culture for each clone to culture viruses.

Assay of recombinant VZV immunogenicity

Solution containing a recombinant VZV is inoculated subcutaneously to small experimental animals such as monkeys, rabbits, guinea pigs and mice, and then these immunized animals are bred. During the breeding period, after inoculation of the virus, he antibody titer of blood is measured weekly, monthly or at certain interval, by partially sampling blood in an amount of approximately 3 ml from the vein of the femoral region in an animal. Measurement of the antibody titer may be accomplished by any of such conventional methods commonly used for immunology and serum diagnosis such as the PEA (passive hemagglutination) method using red blood cells coated with the antigen used for immunity, and the neutralization test method between known viruses in a given amount and the antiserum thereof, in which titer is measured by the CPE method or plaque assay, the maximum dilution of antiserum which neutralizes and reduces the amount of virus by 50%.

Manufacture of live vaccine containing recombinant VZV as effective ingredient

After culturing a recombinant VZV with the use of human diploid cell culture, the resultant culture is purified by, for example, centrifugation and the recombinant VZV fraction is collected. Solutions of amino acid and saccharides are added to, and mixed with, the thus collected fraction, and the resulting solution is diluted to adjust the viral content per dose of live vaccine to at least 1,000 PFU, thus manufacturing the live vaccine. Samples of the live vaccine are subjected to various tests regarding safety, effectiveness and uniformity in accordance with the Minimum Requirements for Biological Products (1989) set out in Notification No. 195 of the Japanese Ministry of Health and Welfare, including the "Dried Attenuated Live Varicella Vaccine" and "Recombinant Precipitated Hepatitis B vaccine (from yeast) to confirm and establish eligibility as a vaccine before use. A vaccine is lyophilized in a vial or an ampoule having a volume of approximately 3 to 30 ml. it is supplied in an airtight state and stored at a temperature lower than 5° C. The vaccine should be used in compliance with the instructions given in the Manual: reconstituting the lyophilized content completely with sterilized distilled water before use, and inoculating 0.5 ml per 1 dose subcutaneously.

Manufacture of diagnostic agent containing recombinant VZV antigen as effective ingredient After culturing a recombinant VZV with the use of human diploid cell culture, the resultant cell is purified by, for example, centrifugation and the recombinant VZV antigen fraction is collected. After Inactivating this antigen through, for example, addition of formalin or heating at 56° C., it is diluted and adjusted with, for example, PBS so as to give an antigen protein content of 1 to 10 μg/ml to prepare a diagnostic agent. This antigen is supplied by sealing in a vial or an ampoule having a volume of 2 to 50 ml in liquid or dried state. The antigen is applicable as the antigen for various techniques of serum diagnosis such as ELISA and PHA, and for the manufacture of antibodies. In the case of a dried product, the dried content is completely reconstituted with distilled water before use.

EFFECTS OF THE INVENTION (1) Supply of muitivalent live vaccine: The recombinant VZV strain made available by the present invention is an attenuated virus with simultaneously expressing a VZV gene and at least one kind of HBV gene, and furthermore, each expression product has an immunogenicity equal to that of the currently used vaccine antigen. The expression ability thereof is genetically stable and satisfactory in the succession of generations of the virus, and this recombinant VZV has safety and effectiveness as a live vaccine. It is therefore applicable in practice as an effective ingredient of a multivalent live vaccine or a multi-function live vaccine in place of the conventional mixed or inactivated ones.

(2) Conversion of inactivated vaccine antigen into live vaccine: Some kinds of antigen have been previously used only for an inactivated vaccine because of the technical restrictions for culturing and purifying them in addition to the risk of adventitious factors, in spite of the facts that such vaccine induces only humoral immunity and can not maintain the immunogenicity for a long period. The present invention, on the other hand, makes it possible to use such antigens for a live vaccine which can induce both humoral and cellular immunity and has a prolonged immunogenicity on a satisfactory level.

(3) Reduction of manufacturing cost of combined vaccine: A conventional combined vaccine has been manufactured by preparing individual ingredients of vaccine separately, and then mixing the prepared ingredients. According to the present invention, it is possible to prepare two or more kinds of different antigens by culturing recombinant VZVs once, thus permitting minimization of the manufacturing cost of vaccine.

(4) The present invention permits mass-production of an HBV antigen which is otherwise difficult to culture or mass-produce.

(5) It is possible to safely manufacture an antigen against a pathogen having a high risk of biohazard.

(6) The recombinant VZV antigen of the present invention, having two or more different kinds of antigen, is useful also as a multivalent diagnostic agent capable of simultaneously determining two or more kinds of pathogens. This genomic DNA of the recombinant VZV is applicable for genetic diagnosis as a chimeric probe consisting of two or more heterogene DNAs.

(7) Contribution to WHO's EPI (Expansion Program of Immunization): As has been described in (1), (2) and (3) above, a multivalent vaccine provided by this invention must bring considerable advantages to mankind with its improved and intensified immunity effects, together with economic merits and labor savings in the manufacture of vaccines, the administration for health and hygiene, the clinical trials, and for individuals to be vaccinated. The present invention, therefore, makes significant contribution to he WHO's proposal for expansion and promotion of vaccination by using a combined or multivalent vaccine.

Now, the present invention is described in detail by means of examples. It is to be noted that the present invention is not limited to these examples.

The phosphate butter saline (PBS) as used in the description of the following examples was prepared as follows: by dissolving 8.0 g NaCl, 0.2 g KCl, 2.9 g $Na_2HPO_4.12H_2O$, 0.2 g $KH_2PO_4$, 0.1 g $CaCl_2$ and 0.1 g $MgCl_2.6H_2O$ in distilled water and adjusted to a volume of 1,000 ml. PBS (−) was separately prepared, which did not contain divalent ions, $CaCl_2$ and $MgCl_2.6H_2$.

EXAMPLE 1

Culture of varicella virus

Human diploid fibroblast, MRC-5, was cultured as the culture host of VZV at 37° C. MEM culture medium [manufactured by Gibco Co. (USA)] was used as the basic culture medium. Immediately before use, aqueous solution of 7% (w/v) $NaHCO_3$ was added to, and mixed with, the culture medium, and pH was adjusted to 7.4 for the multiplication culture medium and to 7.8 for the maintenance culture medium. Then, commercially available fetal bovine serum was further added and mixed so as to give a final concentration of 10% (v/v) for the multiplication culture medium and 3% (v/v) for the maintenance culture medium. The VZV Oka strain (ATCC VR-? 95) seed virus was inoculated to the thus cultured MRC-5 cells at 0.01 MOI (multiplicity of infection) and cultured for three days at 37° C. A maintenance culture medium was used for this culture. During VZV culture, the region of infected cells Gradually expands along with multiplication of VZV. A VZV-infected cell, showing rounding under the microscopic observation, can be detected as an effect known as CPE (cell deterioration effect). By observing the expansion of infected cells under the effect of CPE by means of a microscope, therefore, it is possible to determine the extent of VZV multiplication. VZV culture was completed at the moment when CPE was observed over the entire region of all culture monosheet.

Similarly, Oka strain (WHO Technical Report Series, No. 725, pp. 102-124, 1985) seed virus which was a live varicella vaccine strain was cultured. Five bottles each having a culture area of 210 cm$^2$ were used as culture containers. This Oka varicella vaccine strain was employed in all the following examples.

EXAMPLE 2

Extraction and preparation of VZV genomic DNA

Cells infected with the Oka varcella vaccine strain obtained in the Example 1 were collected. More particularly, after the completion of virus culture, the culture liquid was thrown away, and PBS (−) solution of 0.1% (w/v) EDTA-2 Na in an amount of 16 ml was added to the culture bottles and infected cells were detached from the inner wall surface, which were then pooled. Then the pooled cells were centrifuged at 3,000 rpm for ten minutes at room temperature, and pellets of infected cells were collected. The thus collected cells were then added with 3 ml of 10 mM Tris-HCl (pH: 8.0) containing 0.5% (v/v) NP40 [manufactured by BDH Chemicals Co. (UK)] and 10 mM EDTA-2Na to suspend the cells, and the cells were dissolved by holding for 30 minutes at room temperature. Then, to remove cell fragments, the solution was subjected to centrifugation at 3,000 rpm for 20 minutes at 4° C., and the supernatant was collected. This cycle of operations was repeated three times, and the supernatant was pooled. Then, this supernatant was centrifuged on a SW27 rotor (manufactured by Beckman Instruments Co. [USA]) at 27,000 rpm for one hour at 4° C., to recover pellets. These pellets were suspended in 2 ml of TE solution [10 mM Tris-HCl (pH: 8.0), 1 mM EDTA-2Na]. Then, 2 ml of solubilizing liquid [10 mM Tris-HCl (pH: 8.0), 1% (w/v) SDS, 10 mM EDTA-2Na, 200 μg/ml Proteinase K, and 100 μg/ml RNase A] was added to the suspension to cause reactions at 37° C. overnight. After the completion of reactions, DNA was extracted twice with the use of water-saturated phenol-chloroform-isoamylalcohol (1:1:1) mixed solution in equal amounts, and the water layer was collected. Then, cold ethanol in a double amount was added to, and mixed with, this water layer, and the resulting solution was held overnight at −20° C. to cause precipitation of DNA. After collection by centrifugation, this DNA suspended in 2 ml of TE solution as described above, and the product was provided as a VZV genomic DNA. The concentration of DNA was determined in terms of absorbance $OD_{260}$.

EXAMPLE 3

Preparation of preS2 and HBs DNA fragment of HBV

Plasmid pM1B11 (Japanese Patent Provisional Publication No. 22,098/88) in which preS1-preS2-HBs gene of HBV's subtype adr strain had been cloned in the BamHI site of pBR322, was digested by the use of restriction enzyme HpaII. Then, 0.5% (w/v) agarose gel electrophoresis was applied, and after collecting HpaII fragment, both ends of the fragment were blunt-ended with T4 DNA polymerase.

EXAMPLE 4

Cloning of VZV tk gene

The VZV genomic DNA obtained in the Example 2 was digested with restriction enzyme SacI, and the resultant fragments were subjected to 0.5% (w/v) agarose gel electrophoresis to collect an H fragment (Intervirology, 29, 301-310,1988). This DNA fragment was inserted into SacI site of plasmid pUC12 (Methods in Enzymology, vol. 101, pp. 20-78, Academic Press [USA], 1983), then transferred to E. coli JM109 (ATCC No. 53323), and a plasmid pUC12-tk was prepared. In addition, after digesting pUC12-tk with restriction enzymes EcoRI and FokI, EcoRI-FokI fragments collected through 1.0% (w/v) agarose gel electrophoresis were cloned again into puC12, thus obtaining plasmid pEF6 (see FIG. 1).

EXAMPLE 5

Preparation of chimeric plasmid for constructing recombinant VZV

Figure 2:
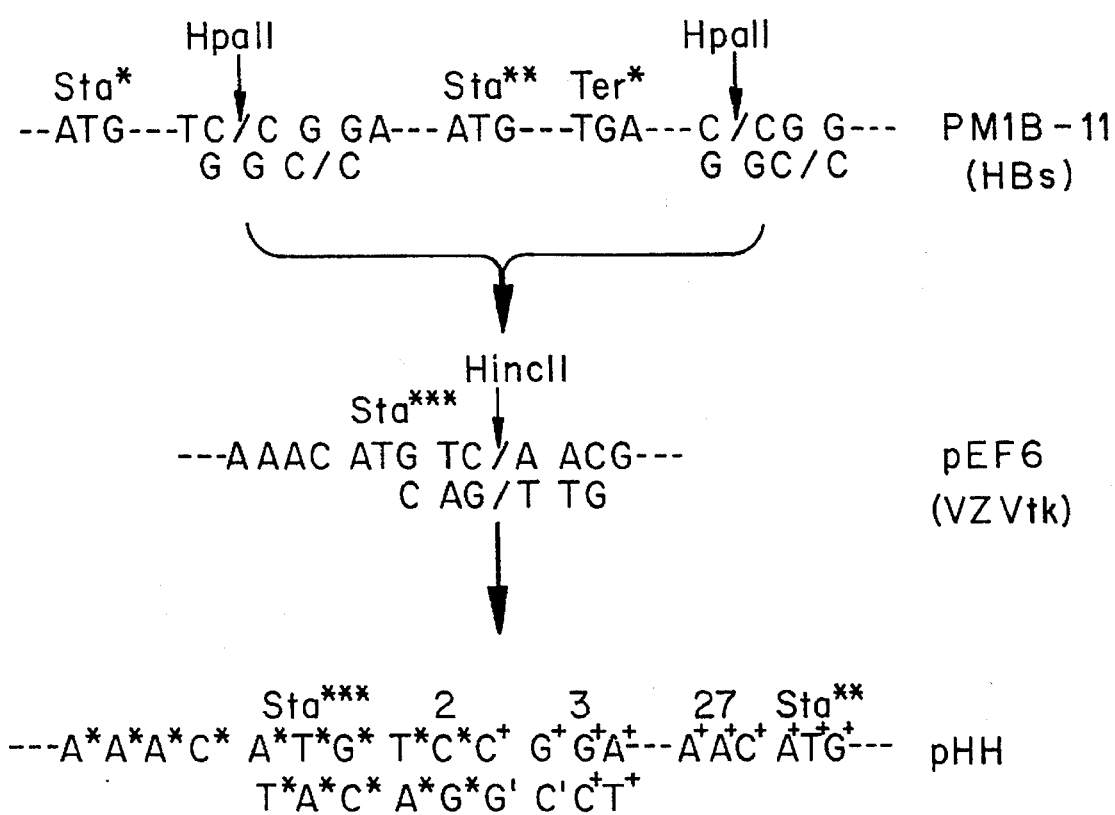
FIG. 2 is a schematic representation of DNA base sequences of the HBV preS2-HBs gene and the VZV tk gene (SEQ ID NO. 1), and of the recombinant sequence of these genes (SEQ ID NO.2) indications: Sta*, starting codon of pre S2 gene; Sta, starting codon of HBs gene; Sta***, starting codon of VZV tk gene: Ter, termination codon of HBs gene; X*, base for VZV tk gene; X', base for flesh end with T4 DNA polymerase; and X⁺, base for HBs gene.

After inserting the HpaII fragment of HBV genomic DNA prepared in the Example 3 into HincII site of the pEF6 tk gene obtained in the Example 4, chimeric plasmid pHH was obtained by transferring it to E. coli JM109 strain (see FIG. 1). The base sequence at the linkage portion of the inserted HBV gene was determined by means of a 7-DEAZA sequencing kit (manufactured by Takara Shuzo Co.; Nucleic Acid Research, 14, 1319, 1988). The result is shown in FIG. 2. In this chimeric pHH, 1,080 base fragments of the HBV's preS2-HBs gene are inserted and linked between the SacI -FokI 4.8 kb fragments of the VZV gene, and the true initiation codon ATG (methionine) and TCC (serine) of HBV preS2 are transcribed and translated in the linked state under the effect of the true promoter and enhancer of the VZV tk gene. In place of the expression of VZV tk gene, 27 amino acids of HBV preS2 and all HBs peptide genes are expressed (see FIGS. 1 and 2).

EXAMPLE 6

Preparation of recombinant VZV

The VZV genomic DNA (2.5 μg/ml) prepared in the Example 2 and the chimeric plasmid pHH (20 μg/ml) prepared in the Example 5 were contransfected to MRC-5 cells cultured in a plastic petridish having a dia. of 60 mm by the calcium phosphate method (Virology, 52, 465-467, 1973) (see FIG. 1). Then, the product of cotransfection was cultured, and infected cells were removed by means of a cylinder from each VZV focus formed through introduction of VZV genome. These infected cells were inoculated to MRC-5 cells cultured in a 25 cm$^3$ plastic flask for each focus for multiplication. At the same time, part of the infected cells were inoculated to MRC-5 cells cultured on a cover slip for each focus and were grown, and the result was observed with a microscope by the immunofluorescence method using anti-HBs monoclonal antibody (manufactured by BML Co. [Japan]). More specifically, cells on each cover slip were washed with PB, and fixed with a mixed solution of cold methanol and cold acetone in equal amounts at −20 C. for five minutes. Then, these cells were dyed with the above mentioned monoclonal antibody of mouse and FITC-labeled anti-mouse IgG antibody. Each of the thus dyed samples was observed by means of a fluorescent microscope to test for the presence of HBs antigenicity and the intensity thereof with the degree of fluorescence as the indicator. As a result, five out of 35 clones (C1-C35) in total were selected as candidates for recombinant VZV. The ratio of recombination was 14.5%. With reference to the test result, cell-free VZVs were prepared from infected cells of the recombinant VZV candidata clones from among the infected cells multiplicated within the flask as described above. The prepared recombinant VZVs were stored at −70° C. until practical use thereof (Journal of General Virology, 61, 255-269, 1982). Then, with the use of the MRC-5 cells cultured in a 60 mm-dia, plastic petridish, a plaque assay was carried out on a single clone (C17) having shown the highest degree of fluorescence from among the above-mentioned candidates for recombinant VZV. A culture medium 199 (manufactured by Difco Co. [USA]) was used for the plaque assay. In a maintenance culture medium prepared in the same manner as in the Example 1, a solid culture medium was prepared by adding and mixing agarose so as to give a final concentration of 0.8% (w/v). This culture medium was used by overlaying on the infected cell monosheet. Dyeing of the infected culture cells was conducted by adding and mixing neutral red to this solid culture medium'so as to give a final concentration of 0.0% (w/v), and further overlaying the thus prepared culture medium. Virus was inoculated after adjusting the VZV concentration so that one to two plaques were formed for each petri dish. Culture was incubated in a 5% (w/v) $CO_2$ gas chamber with the other conditions identical with those in the Example 1. VZV was cloned by hooking up each of the expressed plaques individually by means of a cylinder. One clone (C17-5) from among the obtained recombinant VZVs was inoculated at a rate of one clone-infected cell relative to five to ten non-infected cells, and this was successively conducted from cell to cell for ten generations. From each of the infected cell cultures of the tenth generation, a cell-free recombinant VZV was prepared. A strict selection was applied Go these recombinant VZVs through an immunofluorescence test, and as a result, there were separated 20 cell-free recombinant VZV (FIG. 1) clones that produced HBs antigens. These clones were grouped as rVH Oka strain series, and the twenty strains composing the series were sequentially named in the manner of rVH1 Oka strain, rVH20 Oka strain and rVH30 Oka strain, and from rVH40 Oka strain to rVH20 Oka strain. As all these twenty strains were confirmed to produce HBs antigens to similar extent, production of antigens from such recombinant VZVs is considered genetically stable and satisfactory under viral successive culturing.

In the following Examples, rVH7 Oka strain (rVH17-5 Oka strain, ECACC provisional accession No. V92041523) was used as a typical example of recombinant VZV strains falling under the rVH Oka strain series. The parental strain of rVH7 Oka strain is Oka varicella live vaccine of attenuated VZV, as described in the Examples 1 and 2.

EXAMPLE 7

Restriction enzyme analysis of recombinant VZV genomic DNA

This analysis was carried out by the Southern blot method (Journal of Molecular Biology, 98, 503, 1975). After extracting and preparing genomic DNAs for the Oka varicella live vaccine strain which was he parental strain and the recombinant VZV strain in the same manner as in the Example 2, the DNA fragment available by digesting each DNA with restriction enzyme SacI (SstI) was fractionated by 0.8% (w/v) agarose gel electrophoresis, and the resultant gel was dyed with etidium bromide. Then, a nitrocellulose membrane was placed on top of this gel, and each DNA fraction was transferred to this membrane. After hybridization by an RI-labeled probe, autoradiography was applied. As probes, DNAs of [α-$^{32}$P]dCTP-labeled pM1B11 and pHH were employed. As a result, the original SacI-H fragment was detected in the parental strain, and the SacI-H' fragment, in the recombinant VZV strain. Because the SacI-H fragment contains a VZV tk gene, and no SacI site is present in both HBs and tk gene regions of the recombinant VZV strain, the SacI-H fragment of the parental strain is considered to have shifted to the SacI-H' fragment in the recombinant strain. While the SacI-H fragment of the parental strain reacts only with the pHH probe, the SacI-H' fragment of the recombinant strain is hybridized with pM1B11 and pHH, respectively. The HBs gene is therefore determined to have been inserted into the tk gene of the recombinant VZV genome.

EXAMPLE 8

Detection and identification of HBs antigen produced in cells infected with recombinant VZV strain The rVH7 Oka strain obtained in Example 6 was cultured in the same manner as in Example 1 with the use of five plastic flasks each having a culture area of 150 cm². Resultant supernatants of culture were pooled and centrifuged at 3,000 rpm for 20 minutes at 4° C. Infected cells were detached from the inner wall surface of the culture flasks with rubber scrubber and suspended in PBS.

(1) Measurement of quantity of produced HBs antigen: Further centrifugation was applied at 27,000 rpm for three hours at 4° C. to 35 ml of the above-mentioned supernatant, and pellets were collected, which were then suspended in 0.2 ml of PBS that formed the culture supernatant fraction of the recombinant strain. In contrast, approximately 10⁶ infected cells as described above were suspended in 1 ml of PBS. After destroying the cells by ultrasonic wave (20 kHz, 150 mA, 4 seconds), the suspension was centrifuged at 3,000 rpm for 20 minutes at 4° C., and the resulting supernatant was collected as the recombinant strain infected fraction. For the both fractions, the HBs antigen titer was measured by the application of the RPHA (reverse passive hemagglutination) test using cells coated with anti-HBs serum. For this test, a commercially available test kit (manufactured by Midori Juji Co. [JAPAN]) was used. For purpose of comparison, there were used also a non-infected cell fraction and a parental strain infected cell fraction prepared from approximately 10⁶ cells in the same manner as above, and an HBs antigen produced in yeast (Japanese Patent Provisional Publication No. 22,098/88). These samples were diluted in two stages and subjected to measurement. The results are shown in Table 1. Table 1 permits estimation that the quantity of produced HBs is 10 µg/ml for the infected cell fraction resulting from culture of the recombinant VZV strain and 4 µg/ml for the culture supernatant fraction (23 ng/ml for the original culture supernatant before concentration.)

TABLE 1

Measurement of HBs antigen expressed in the recombinant VZV-infected culture by the RPHA test

| Antigen | RPHA value(*) |
| --- | --- |
| Non-infected cell fraction (10⁶ cells/ml) | 1 |
| Parental VZV-infected cell fraction (10⁶ cells/ml) | 1 |
| Recombinant VZV-infected culture supernatant (concentrated 175 times) | $2^5$ |
| Recombinant VZV-infected cell fraction (10⁶ cells/ml) | $2^6$ |
| HBs antigen made in yeast (250 µg/ml) | $2^{12}$ |

(Note) *Maximum dilution multiples of antigen showing RPHA positivity.

(2) Detection of HBs antigen by immunofluorescence method: Presence of any produced HBs antigen was detected in the above-mentioned recombinant VZV-infected cells by the application of the immunofluorescence method using the monoclonal antibody of HBs antigen as described in the Example 6. The result permitted confirmation of the production of HBs antigen within the infected cytoplasm.

(3) Confirmation of HBs antigen in culture supernatant by electron microscope: The above-mentioned culture supernatant was centrifuged at 5,000 rpm for 20 minutes, and then PEG (polyethylene glycol) 6,000 was added to, and mixed with, this supernatant so as to give a final concentration of 10% (w/v) to form a precipitate. Then, precipitate pellets collected through low-speed centrifugation were suspended in TEN liquid [20 mM Tris-HCl (pH; 7.4), 1 mM EDTA-2Na, 150 mM Nacl], and then, this suspension was subjected to CsCl density gradient equilibrium centrifugation twice by means of an SW27 rotor. With the use of a discontinued gradient comprising densities of 1.15, 1.25 and 1.4 g/cm$^3$ in the centrifugal tube, the precipitate suspension was overlaid on this CsCl solution, and centrifugation was applied at 23,000 rpm for 20 hours at 4° C. After the completion of centrifugation, the CsCl solution was fractionated, and the HBs antigen fraction was determined through the above-mentioned RPHA test. The resultant HBs antigen fraction was mixed with TEN liquid, and after adjusting density to 1.2 g/cm$^3$ by CsCl, was further centrifuged by an SW41 at 33,000 rpm for 40 hours at 4° C. After the completion of the centrifugation, the CsCl solution was fractionated. The HBs antigen fraction was sampled and diluted, and after overlaying it on a 10% (w/v) sucrose cushion, was centrifuged by an SW41 rotor at 40,000 rpm for three hours at 4° C. The resultant pellets were suspended in PBS and observed through an electron microscope. As a result, many particles having a dia. of 20 to 30 nm were detected in the final purified HBs fraction. It is judged from this result that particle-shaped HBs antigen is secreted from infected cells.

Figure 3:
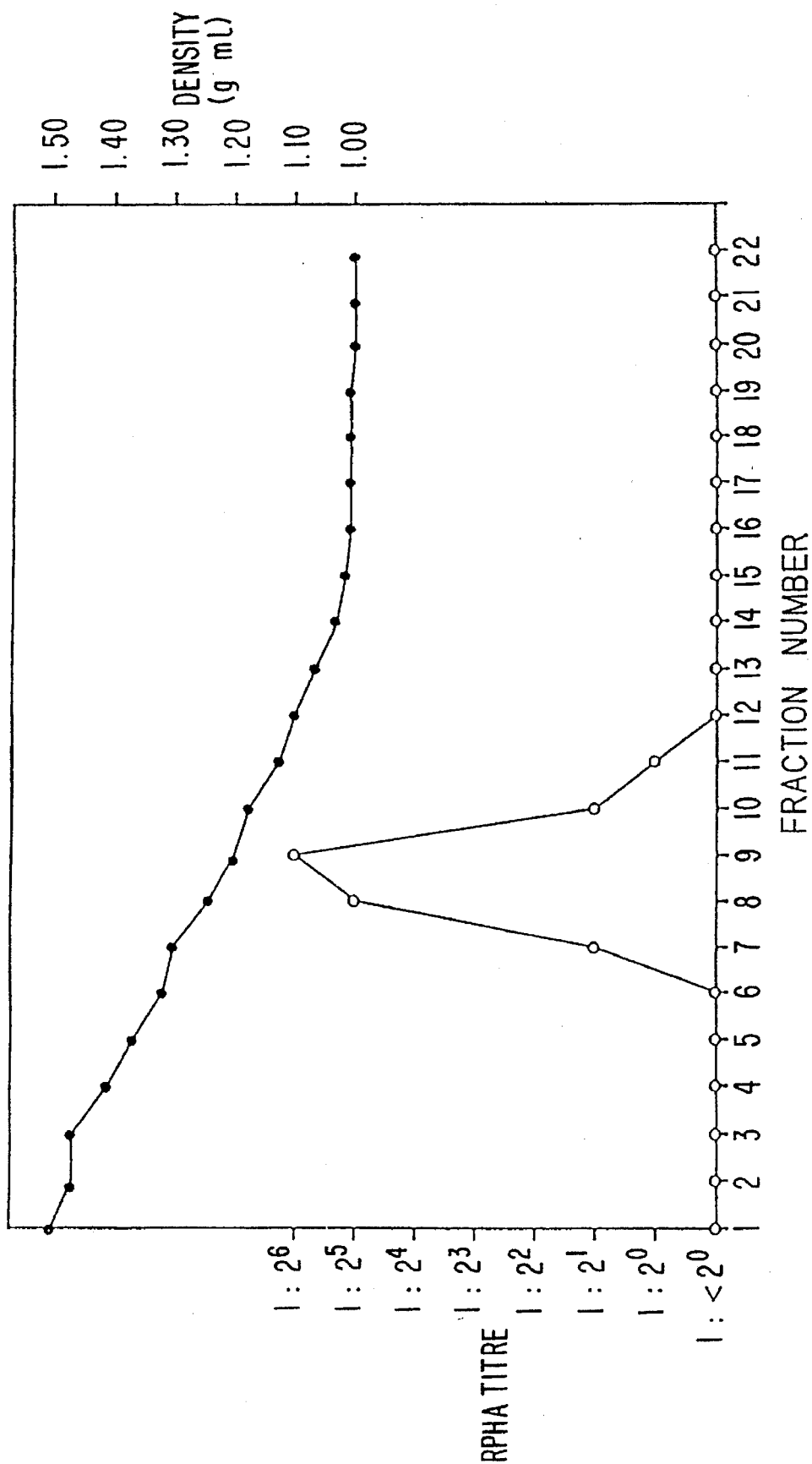
FIG. 3 shows purification of HBs secreted from cells infected with the recombinant VZV of the present invention. HBs antigen secreted from infected cells was concentrated and subjected to equilibrium centrifugation in CsCl. The density (g/ml) of the fraction was monitored by measuring the volume and weight, and titers of HBs antigen were assayed by the RPHA test.

(4) Measurement of density of HBs antigen in culture supernatant; A portion of the purified HBs fraction used in the above-mentioned electron microscopic observation was fractionated by CsCl density gradient equilibrium centrifugation of a density of 1.2 g/cm$^3$ at 33,000 rpm for 40 hours at 4° C. with the use of an SW41 rotor. Density was calculated for fractions by measuring the volume and the weight, and at the same time, the HBs antigen titer was measured by an RPHA test. The results showed a density of the purified HBs fraction of 1.20 g/cm$^3$, which represents the peak of the HBs activity (see FIG. 3).

EXAMPLE 9

Identification of VZV and HBs antigens of the recombinant VZV strain

MRC-5 cells were cultured on three petridishes having a dia. of 100 mm in the same manner as in the Example 1. On one of the three dishes, rVH7 Oka strain was inoculated, and the parental strain thereof was inoculated to the cells on one of the remaining dishes. For cell culture on the last dish, no virus was inoculated, but the dish was used for preparing antigen for comparison. These cells were cultured for four hours in the same manner as in the Example 1, by means of a basic culture medium prepared by adding [$^{35}$S] methionine of 50 μCi/ml and cysteine to an MEM culture medium not containing methionine. Then, the cells were detached and after dissolving the cells into an RIPA buffer solution [20 mM Tris-HCl (pH; 8.0), 1% (w/v) Triton x-100, 0.1% (w/v) SDB, 150 mM NaCl, and 1 mM phenylmethyl-sulfonyl fluoride], centrifuged at 35,000 rpm for an hour. The supernatant hereof was sampled. The supernatant was centrifuged at 3,000 rpm for 20 minutes to collect the supernatant thereof. Each of the six kinds of supernatant was mixed with anti-VZV guinea-pig serum (Virology, 156, 423–426, 1987), to cause the immunoprecipitation reaction. Immune complex formed by these reaction systems were separated individually by column chromatography with protein A Cepharose CL-4B [manufactured by Pharmacia LKB (Sweden)]. Immune complex was similarly formed also between an anti-HBs rabbit serum prepared with the use of an HBs antigen (Japanese Patent Provisional Publication No. 22,098/88) and these six kinds of supernatant, and separated.

Then, each of these immune complex was subjected to autoradiography after SDS-PAGE electrophoresis. As a result, VZV polypeptide was detected simultaneously in the infected cells of both the parental strain and the recombinant strain. The 26 k and 30 k HBs antigens were detected only in the infected cells of the recombinant strain. In the culture supernatant of he recombinant strain, the HBs antigens secreted by the infected cells of the recombinant strain described in the Example 8 were identified as both the 30 k and 35 k polypeptides. It is judged from this identification that the 28 k and 30 k HBs antigens synthesized within the infected cells undergo modification and processing, while being secreted into the culture supernatant, and become the 30 k and 35 k HBs antigens.

EXAMPLE 10

Manufacture of live vaccine containing recombinant VZV as effective ingredient

After inoculating the rVH7 Oka strain seed virus obtained in the Example 6 to MRC-5 cell cultured in twenty bottles each having a culture area of 210 cm$^2$, culture was conducted in the same manner as in the Example 1. After the completion of the culture, the culture medium was removed, and the infected cells in the bottles were washed twice with 200 ml of PBS(−). Then, 20 ml of 0.03% (w/v) EDTA-3Na were added to the infected cells in the bottles, the cells being detached from the inner walls of the bottles and suspended. The infected cell suspension in the bottles was pooled, centrifuged at 2,000 rpm for ten minutes at 4° C., and pellets of the infected cells were collected. The pellets were suspended again in 100 ml of PBS(−), and freeze-thawings was done once. Then, after conducting an ultrasonic treatment (20 kHz, 150 mA, 0.3 seconds/ml) in an ice-water bath, a centrifugation was applied at 3,000 rpm for 20 minutes at 4° C. The supernatant containing cell-free virus was prepared as the original virus suspension of live vaccine. From this original virus suspension, 30 ml were sampled for test, and saccharose and gelatin hydrolysis products dissolved in PBS(−) were added to, and mixed with, the remaining 70 ml of original virus suspension as the vaccine stabilizer so as to give final concentrations of 5% (w/v) and 2.5% (w/v) to prepare a final bulk of live vaccine in an amount of 140 ml. After sampling 30 ml for test from this final bulk, the remaining bulk was filled into vials each having a capacity of 3 ml by 0.5 ml. After freeze-drying, the bottles were filled with nitrogen gas and plugged with rubber stoppers to seal airtightly the bottles. These subdivided bottles of live vaccine are stored at 4° C., and distilled water for injection in an amount of 0.5 ml is added to completely reconstitute the dried content immediately before use. In contrast, 20 bottles of the sampled original virus suspension, final bulk and subdivided product were subjected to various tests. The tests were carried out in conformity to the Minimum Requirements for Biological Products (1989) "Dried Attenuated Live Varicella Vaccine" prescribed in the Japanese Ministry of Health and Welfare Notification No. 195, and with reference to another standard "Recombinant Precipitated Hepatitis B Vaccine (originating from yeast)" set forth in the same Notification, to confirm safety, effectiveness and uniformity and to establish eligibility as a live vaccine. As a result of these tests, the above-mentioned subdivided product had a virus content of 2×10$^4$ PFU/0.5 ml and was qualified in the various tests specified in the standard. It has therefore been practically used since then as a suitable live vaccine.

EXAMPLE 11

Manufacture of recombinant VZV antigen as diagnostic agent

After inoculating the rVH7 Oka strain seed virus obtained in the Example 6 to MRC-5 cell cultures contained in twenty bottles each having a culture area of 210 cm², culture was conducted in the same manner as in the Example 1. After the completion of culture for a day, culture liquid was discarded, and the infected cells in the bottles were washed twice with 200 ml of PBS(−). Then, Phenol Red was removes from Culture Medium 199 [manufactured by Difco Co. (USA)] and it was poured into these bottles, and culture was continued at 37° C. for another three days. After the completion of the culture, culture liquid was sampled from bottles and pooled. The pooled liquid was then centrifuged at 3,000 rpm for 20 minutes, and the supernatant was concentrated in volume to 1/20 by means of a Minitan Ultra-Filter MW10000 [manufactured by Millpore (USA)]. Then, the concentrated liquid was heated at 56° C. for 30 minutes to inactivate the virus. The liquid was diluted with PBS so that the content of the recombinant VZV antigen protein in the thus obtained liquid became 5 μg/ml and the resultant liquid was poured into ampoules each having a capacity of 3 ml by 2 ml. The ampoules were sealed by melting and used as a diagnostic agent of chickenpox and hepatitis B.

EXAMPLE 12

Assay of immunogenicity of recombinant live vaccine containing recombinant VZV as an effective ingredient Immunogenicity of the recombinant varicella live vaccine strain manufactured in the Example 10 was measured in guinea pigs. For comparison, the following five kinds of vaccine were employed: the commercially available dried attenuated live varicella vaccine which was the parental vaccine (prepared by The Research Foundation for Microbial Diseases of Osaka University) a recombinant precipitated hepatitis B vaccine [one manufactured under Japanese Patent Provisional Publication No. 22,098/88, and the other, manufactured by Merck Co. (USA)] and antigens for comparison prepared through a similar process to that in the Example 10 from MRC-5 non-infected cells. Each of these vaccines was subcutaneously inoculated to three guinea pigs of a three weeks old average body weight of 250 g. The recombinant strain and parental strain vaccines were diluted with PBS(−) so that the amount of inoculation became 3,000 PFU or 2,000 PFU/dose. The hepatitis B vaccines were inoculated so as to give an amount of HBs antigen of 10 μg/animal. Four six and eight weeks after the vaccine inoculation, blood was partially collected from the vein of the femoral region of each of the inoculated animals to measure the antibody titer of blood. For the measurement of the antibody titer the neutralization test method (Journal of General Virology 61, 255–269, 1982) was adopted or VZV and the PHA (passive hemagglutination ) test kit (manufactured by the Chemical and Serum Therapy Research Laboratory) using cells coated with HBs antigen for HBs. The results are shown in Tables 2 and 3. The parental strain and the recombinant strain vaccines induced the VZV antibody on the same level, whereas an HBs antibody was detected only in the recombinant strain vaccine inoculation (see Table 2). Furthermore, the immunogenicity of the recombinant strain vaccine against HBs was equal to that of the commercially available hepatitis B vaccine (see Table 3). It is judged from these results that the recombinant strain vaccine has excellent immunogenicity against both the VZV and HBs antigens.

TABLE 2

Antibody response of guinea-pigs immunized by VZV carental strain and recombinant strain vaccines against VZV and HBs antigens

| Immunogen | Anti-VZV antibody titer | Anti-HBs antigen antibody titer |
|---|---|---|
| VZV-HBs recombinant strain vaccine | | |
| Subject No. 1 | 8 | 6 |
| No. 2 | 4 | 4 |
| No. 3 | 8 | 4 |
| VZV carental strain vaccine | | |
| Subject No. 4 | 4 | <1 |
| No. 5 | 8 | <1 |
| No. 6 | 8 | <1 |
| Non-infected cell antigen for comparison | | |
| Subject No. 7 | <1 | <1 |
| No. 8 | <1 | <1 |
| No. 9 | <1 | <1 |

(Note 1) Amount of subcutaneous inoculation of vaccine: 2,000 PFU of cell-free virus/animal.
(Note 2) Measurement of antibody titer: conducted by collecting blood four weeks after vaccine inoculation.
(Note 3) method of measurement of antibody titer: the neutralization test was adopted for VZV, and PHA, for HBs.
(Note 4) Figures: Maximum dilution of immunized rabbit serum showing positive antibody reaction.

TABLE 3

Comparison of immunity response of guinea Pigs inoculated with recombinant VZV strain vaccine and existing recombinant HBs vaccine against HBs

| Immunogen | Test 1* 4 weeks | Test 1* 6 weeks | Test 1* 8 weeks | Test 2* 4 weeks |
|---|---|---|---|---|
| VSV-HBs recombinant vaccine | | | | |
| Subject No. 10 | 32 | 64 | 64 | 32 |
| No. 11 | 32 | 64 | 64 | 32 |
| No. 12 | 64 | 64 | 64 | 128 |
| Alum precipitation hepatitis B vaccine | | | | |
| Subject No. 13 | 32 | 32 | 32 | 128 |
| No. 14 | 128 | 128 | 128 | 32 |
| No. 15 | 32 | 32 | 32 | 64 |
| VZV parental strain vaccine | | | | |
| Subject No. 16 | <1 | <1 | <1 | NT |
| No. 17 | <1 | <1 | <1 | NT |
| No. 16 | <1 | <1 | <1 | NT |

(Note 1) Amount or subcutaneous inoculation of vaccine:
*In test 1,10 μg HBs antigen/animal, using a recombinant HBs vaccine (Japanese Patent Provisional Publication No. 22,098/68);
*In test 2, 10 μg HBs antigen/animal, using a recombinant HBs vaccine (manufactured by Merck)
*In both tests 1 and 2, 3,000 PFU cell-free virus/animal, using both the VZV recombinant and VZV parental strain vaccines;
(Note 2) Measurement of antibody titer: After immunizing, blood was sampled following the lapse of weeks as listed in the table, and measurement was based on PHA.
(Note 3) Figures: Maximum dilution of immunized rabbit serum showing positive antibody reaction;
(Note 4) NT: no test was effected.

What is claimed is:

1. A recombinant varicella-zoster virus live vaccine, comprising the genomic DNA of the Oka varicella vaccine strain and the HpaII fragment of the hepatitis B surface antigen gene, wherein said fragment is inserted into the HincII site of the thymidine kinase gene of said genomic DNA so that the 5'-end of said fragment is linked with the starting codon of said thymidine kinase gene in a correct reading frame, and the hepatitis B surface antigen gene is expressed under sole control of said thymidine kinase gene promoter.

2. rVH17-5 Oka strain (ECACC No. V92041523), a representative clone of the recombinant varicella-zoster virus of claim 1.

3. The genomic DNA of the recombinant varicella-zoster virus as claimed in claim 1.

4. A live vaccine containing an immunizing dose of the recombinant varicella-zoster virus as claimed in claim 1.

5. A method for constructing a recombinant varicella-zoster virus live vaccine, which comprises inserting the HpaII fragment of the hepatitis B surface antigen gene into the HincII site of the thymidine kinase gene of the Oka varicella vaccine strain, so that the 5'-end of said fragment is operably linked with the starting codon of said thymidine kinase gene in a correct reading frame.

* * * * *